United States Patent [19]

Martin et al.

[11] Patent Number: 5,156,592
[45] Date of Patent: Oct. 20, 1992

[54] PRE-CURVED DUAL LUMEN CATHETER

[76] Inventors: Geoffrey S. Martin, 159 Donnelly Drive, Mississauga, Ontario, Canada, L5G 2M3; Jonathan E. Last, 3173 Keynes Crescent, Mississauga, Ontario, Canada, L5N 2Z9

[21] Appl. No.: 680,449

[22] Filed: Apr. 4, 1991

[30] Foreign Application Priority Data

Apr. 4, 1990 [CA] Canada ................... 2013877

[51] Int. Cl.$^5$ .......................... A61M 3/00
[52] U.S. Cl. ...................... 604/43; 604/175; 604/282
[58] Field of Search ............ 604/28, 29, 43-45, 604/174, 175, 51-53, 93, 264, 280, 281, 282

[56] References Cited

U.S. PATENT DOCUMENTS

| | | | |
|---|---|---|---|
| 4,300,550 | 10/1981 | Gandi et al. | 128/207.18 |
| 4,687,471 | 8/1987 | Twardowski et al. | 604/175 |
| 4,772,269 | 9/1988 | Twardowski et al. | 604/175 |
| 4,773,431 | 9/1988 | Lodomirski | 128/769 |
| 4,808,156 | 2/1989 | Dean | 604/43 |
| 4,895,561 | 1/1990 | Mahurkar | 604/43 |
| 5,053,023 | 10/1991 | Martin | 604/280 |
| 5,057,073 | 10/1991 | Martin | 604/43 |
| 5,058,595 | 10/1991 | Kern | 128/662.06 |
| 5,098,413 | 3/1992 | Trudell et al. | 604/281 |

FOREIGN PATENT DOCUMENTS

| | | | |
|---|---|---|---|
| 1092927 | 1/1981 | Canada | 604/43 |
| 146777 | 1/1984 | Denmark | |
| 0081724 | 6/1983 | European Pat. Off. | |

*Primary Examiner*—John D. Yasko
*Assistant Examiner*—Adam J. Cermak
*Attorney, Agent, or Firm*—Rogers & Scott

[57] ABSTRACT

A dual lumen catheter especially for use in prolonged access haemodialysis, which meets the requirements of flexibility and softness for prolonged access in a vein, and which is shaped to include a curved portion to be placed between the tunnel and the subclavian vein.

19 Claims, 2 Drawing Sheets

PRE-CURVED DUAL LUMEN CATHETER

This invention relates to a dual lumen catheter suitable for longer term insertion into a vein of a patient for use in haemodialysis treatments, and more particularly to such a catheter useful for insertion in the subclavian vein using a conventional tunnelling technique Dual lumen catheters have been available for many years for a variety of medical purposes. It is only in recent years however, that such catheters have been developed for use in procedures such as haemodialysis.

Initially a surgical cut-down technique was used universally for vascular catheter access and this technique can be traced back to the 17th century. It is only as recently as about 1952 that a new approach to vascular access was taught when an article was published by Dr. Sven Ivar Seldinger resulting from a presentation made at the Congress of the Northern Association of Medical Radiology at Helsinki in Jun. of 1952. The technique is still current and essentially involves the use of a hollow needle to make an initial puncture, a very flexible wire is then entered through the needle and positioned in the vessel, and then the needle is withdrawn and a catheter is entered percutaneously over the wire which is itself later withdrawn. With this technique it became possible to make less traumatic vascular access and this has now become an accepted method of performing access in numerous medical techniques. One of these techniques which has been the subject of much research and development is haemodialysis.

Haemodialysis can be defined as the temporary removal of blood from a patient for the purpose of extracting or separating toxins therefrom and the return of the cleansed blood to the same patient. Haemodialysis is indicated in patients where renal impairment or failure exists, that is, in cases where the blood is not being properly or sufficiently cleansed, (particularly to remove water) by the kidneys.

In the case of chronic renal impairment or failure, haemodialysis has to be carried out on a repetitive basis. For example, in end stage kidney disease where transplantation of kidneys is not possible or for medical reasons is contra-indicated, the patient will have to be dialysed about 100 to 150 times per year. This can result in several thousand accesses to the blood stream to enable the active haemodialysis to be performed over the remaining life of the patient.

Towards the end of 1960, Dr. Stanley Shaldon and colleagues developed, in the Royal Free Hospital in London, England, a technique for haemodialysis by percutaneous catheterization of deep blood vessels, specifically the femoral artery and vein. The technique was described in an article published by Dr. Shaldon and his associates in the Oct. 14th, 1961 edition of The Lancet at Pages 857 to 859. Dr. Shaldon and his associates developed single lumen catheters having tapered tips for entry over a Seldinger wire to be used in haemodialysis. Subsequently, Dr. Shaldon began to insert single lumen inlet and outlet catheters in the femoral vein and this was reported in the British Medical Journal of Jun. 19th, 1963. The purpose of providing both inlet and outlet catheters in the femoral vein was to explore the possibility of a "self-service" approach to dialysis. Dr. Shaldon was subsequently successful in doing this and patients were able to operate reasonably normally while carrying implanted catheters which could be connected to haemodialysis equipment periodically.

Some use was made of a flexible dual lumen catheter inserted by surgical cut-down as early as 1959. An example of such a catheter is that of McIntosh and colleagues which is described in the Journal of the American Medical Association of Feb. 21, 1959 at pages 137 to 138. In this publication, a form of dual lumen catheter is made of non-toxic vinyl plastic and described as being inserted by cut-down technique into the saphenous vein to the inferior vena cava.

The advantage of dual lumen catheters in haemodialysis is that only one vein access need be affected to establish continued dialysis of the blood, because one lumen serves as the conduit for blood flowing from the patient to the dialysis unit and the other lumen serves as a conduit for treated blood returning from the dialysis unit to the patient. This contrasts with prior systems where either two insertions were necessary to place the two catheters as was done by Dr. Shaldon, or a single catheter was used with a complicated dialysis machine which alternately removed blood and returned cleansed blood through a single lumen.

The success of Dr. Shaldon in placing catheters which remained in place for periodic haemodialysis caused further work to be done with different sites. Dr. Shaldon used the femoral vein and in about 1977 Dr. P. R. Uldall, in Toronto Western Hospital, Canada, began clinical testing of a subclavian catheter that would remain in place between dialysis treatments. An article describing this was in "Dialysis and Transplantation", Volume 8, No. 10, in Oct. 1979. Subsequently Dr. Uldall began experimenting with a coaxial dual lumen catheter for subclavian insertion and this resulted in Canadian Patent No. 1,092,927 which issued on Jan. 6, 1981. Although this particular form of catheter has not achieved significant success in the market-place, it was the forerunner of dual lumen catheters implanted in the subclavian vein for periodic haemodialysis.

The next significant step in the development of a dual lumen catheter for haemodialysis is Canadian Patent No. 1,150,122. This catheter avoided the disadvantages of the Uldall structure and achieved some commercial success.

A subsequent development is shown in U.S. Pat. No. 4,451,252 to Martin, one of the inventors of the present invention. The structure shown in this patent utilizes the well known dual lumen configuration in which the lumens are arranged side-by-side separated by a diametric septum. The tip is formed to make it possible to enter a Seldinger wire through one of the lumens and to use this wire as a guide for inserting the catheter percutaneously. This type of structure is also shown in a European Patent Application to Edelman published under No. 0 079 719, and in U.S. Pat. Nos. 4,619,643, 4,583,968, 4,568,329, 4,543,087, 4,692,141, and U.S. Pat. No. 272,651.

The requirements for a catheter suitable for prolonged access lead to difficulties. While a soft and flexible catheter would be acceptable insofar as it follows vein contours and has minimal resistance to deflection in the flow of blood, such a catheter can be prone to kinking and flexing. This is particularly problematical when the tunnelling procedure is used for inserting such a catheter into a subclavian vein. Because of the physical limitation of the access site, the catheter must extend in the tunnel along a path generally parallel with the vein so that the catheter body must have a curved portion between a proximal portion in the tunnel and a distal portion in the vein. While a conventional soft catheter will bend readily to take up the necessary curvature, the stresses created in the catheter wall and the pressures applied by tissue can combine to deform the catheter material locally beyond the elastic limit resulting in 'kinking' of the body. Once a kink is made, the body tends to remain in this condition and the catheter is no longer useful. This tendency towards kinking makes it undesirable to use prior art catheters in this way and yet many surgeons prefer to use the tunnel technique.

It is therefore among the objects of the present invention to provide a catheter for prolonged access which is particularly useful for placement in the subclavian vein using a tunnelling technique. Also, it is an object to provide a method of manufacturing such a catheter.

In one of its aspects, the invention provides a dual lumen catheter especially for use in prolonged access haemodialysis, which meets the requirements of flexibility and softness for prolonged access in a vein, and which is shaped to include a curved portion to be placed between the tunnel and the subclavian vein.

In another of its aspects the invention provides a flexible catheter for prolonged vascular access having an elongate flexible and tubular body including a proximal portion, and distal portion, and a permanently curved portion linking the proximal and distal portions. The curved, proximal and distal portions lie naturally in essentially the same plane with the angle contained between the proximal and distal portions being less than 90° and a septum extends continuously through the portions and lies substantially at right angles to the aforementioned plane thereby dividing the tubular body into generally D-shaped intake and outlet lumens. Intake and outlet tubes are coupled to the proximal portion at a proximal end of the body remote from the curved portion to receive incoming fluid from the intake lumen and to supply outgoing fluid to the outake lumen. A tip is formed on the distal end of the distal portion and includes at least one intake opening for receiving incoming fluid and at least one outlet opening for returning the outgoing fluid.

These and other aspects of the invention will be better understood with reference to the drawings, in which.

Figure 1:
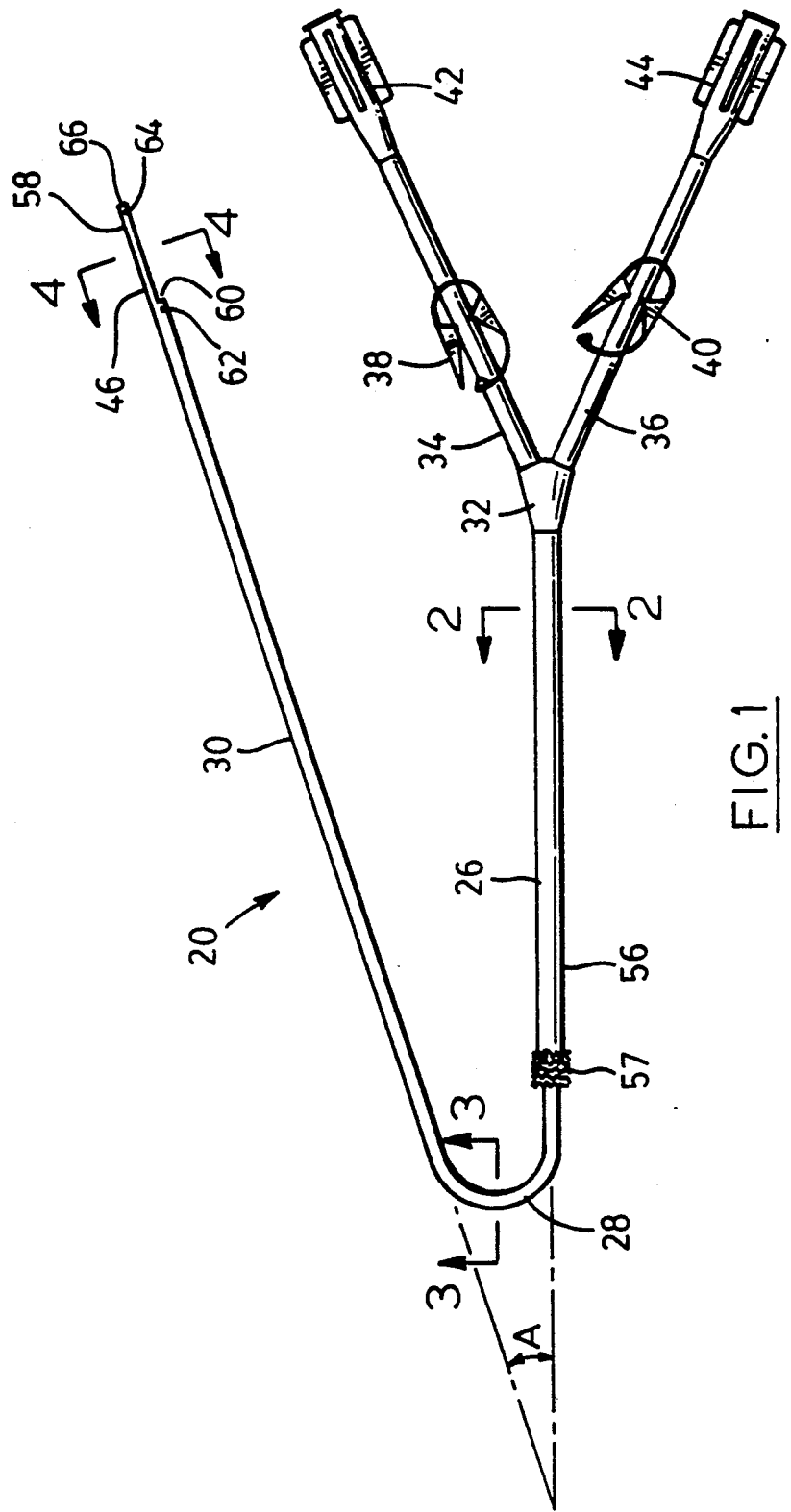
FIG. 1 is a side view of a preferred embodiment of a catheter according to the invention.

Reference is first made to FIG. 1 which illustrates a catheter designated generally by the numeral 20 and including a body 24 consisting of a proximal portion 26 leading to a curved portion 28 which in turn leads to a distal portion 30. The body has at its proximal end a coupling 32 to respective intake and outlet tubes 34, 36 which are equipped with conventional clamps 38, 40 and luer connectors 42, 44. At the distal end, the body has a tip 46 which will be described in more detail later.

It will also be seen in FIG. 1 that in the natural condition after manufacture, the proximal and distal portions 26, 30 lie naturally in a plane which also contains the intake and outlet tubes 34, 36, and that the angle subtended by the portions 26, 30 is the angle "A". This angle in the embodiment shown, is about 20°. As will be described, the angle can be within any range but is preferably in the range 0°–20° and certainly less than 90° for most uses. Although the angle shown in FIG. 1 is 20°, the angle shown is predicated primarily by the need to illustrate the catheter and in practice, the angle in its preferred form, would be less that 20°.

It should also be mentioned that because the catheter is very flexible it will bend even while being handled. The term "naturally in a plane" is intended to describe the shape when the catheter is free of any bending stresses.

The cross sections of the various parts of the body 24 will now be described. Firstly, with reference to FIG. 2, it can be see that the proximal portion consists of a tubular extrusion 47 which is circular in cross section and defined by an outer wall 48 and includes an internal central septum 50 dividing the tubular extrusion into an intake lumen 52 and an outlet lumen 54. The septum 50 lies at right angles to a plane containing the body 24 which, as drawn, means that the septum lies at right angles to the plane of the paper.

The extrusion 47 is surrounded closely by a sleeve 56 which enhances the rigidity of the portion 26 for reasons which will be explained. Returning to FIG. 1, the sleeve 56 terminates inside a porous cuff 57 which is used to permit body tissue to attach to the catheter during prolonged access for better securing the catheter to the insertion site.

Figure 2:
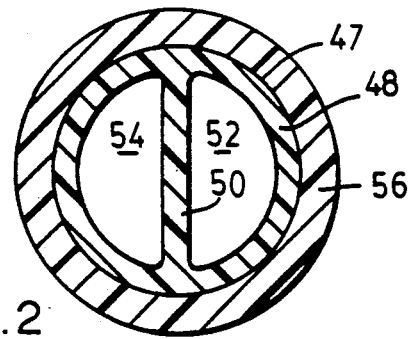
FIG. 2 is a sectional view (drawn to a larger scale) on line 2—2 of FIG. 1 and showing a cross section of a proximal portion of the catheter body.
Figure 3:
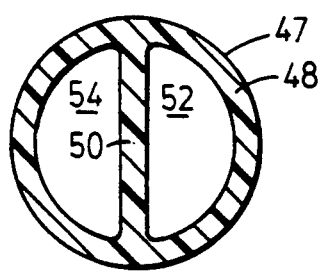
FIG. 3 is a sectional view (also drawn to a larger scale) on line 3—3 of FIG. 1 and showing a curved portion of the catheter body.

The extrusion 47 described in FIG. 2 continues beyond the cuff 57 and is used in the formation of the curved portion 28 and the distal portion 30, as well as in the tip 46. As seen in FIG. 3, the cross section in the curved portion is similar to that shown in FIG. 2 with the exception that there is no outer sleeve. Consequently the portion 28 has the natural soft, very flexible characteristics desirable for prolonged access in a vein. This softness would of course lead to the possibility of kinking and obstruction of the lumens 52, 54 but for the integrity of the curved portion achieved by the method of manufacture to be described with reference to FIGS. 5 and 6.

Figure 4:
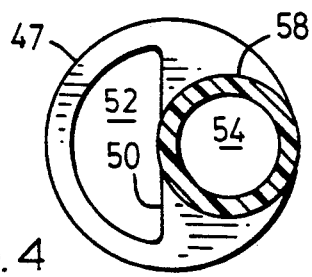
FIG. 4 is a sectional view (again drawn to a larger scale) on line 4—4 of FIG. 1 and showing a tubular extension forming part of a tip at a distal end of the body.

The cross section at FIG. 3 is common also for the distal portion 30 but at the tip 46, the cross section changes into a cylindrical extension 58 having a cross section shown in FIG. 4. This tip is manufactured by removing a portion of the wall 48 (FIG. 2) to expose the septum 50 and leave the part of the wall combining with the septum to form the lumen 52. Using a round mandrel and heat, the D-shaped lumen is changed into a circular cross section thereby making the tip smoother and ensuring that there are no irregularities which would be undesirabe in the vein.

The distal extremity of the intake lumen is an opening 60 which is simply the exposed end of the lumen 54. This opening is augmented by a pair of side openings 62 (one of which is seen) to improve blood flow into the lumen 54. Similarly, after deformation to form the tubular extension 58, the wall is punctured to form openings 64 for enhancing flow which also takes place through an end opening 66 at the very end of the tip 46.

The extrusion 47 (FIG. 2) is of soft medical grade polyurethane having minimal resistance to deflection but nevertheless, after formation of the curved portion 28, having a tendency to remain in the shape shown in FIG. 1. Because the septum lies at right angles to the general plane containing the body, movement of the proximal and distal portions 26, 30 away from one another or towards one another can be accommodated in the material in the curved portion 28 because the septum lies along a plane of minimal stress, on the neutral axis of the extension. Also the septum tends to help with the integrity of the structure because any tendency to flatten the curved portion by applying load on the outer extremeties of the septum will be resisted by the septum. Similarly, if a load is applied at right angles to the septum, this will tend to make the tubing oval and this is resisted by the septum which is then in tension. Consequently the septum tends to aid in resisting forces applied to deform and flatten the tube. The resulting catheter is capable of being used in tunnelling procedures. The method of manufacture will next be described.

Figure 5:
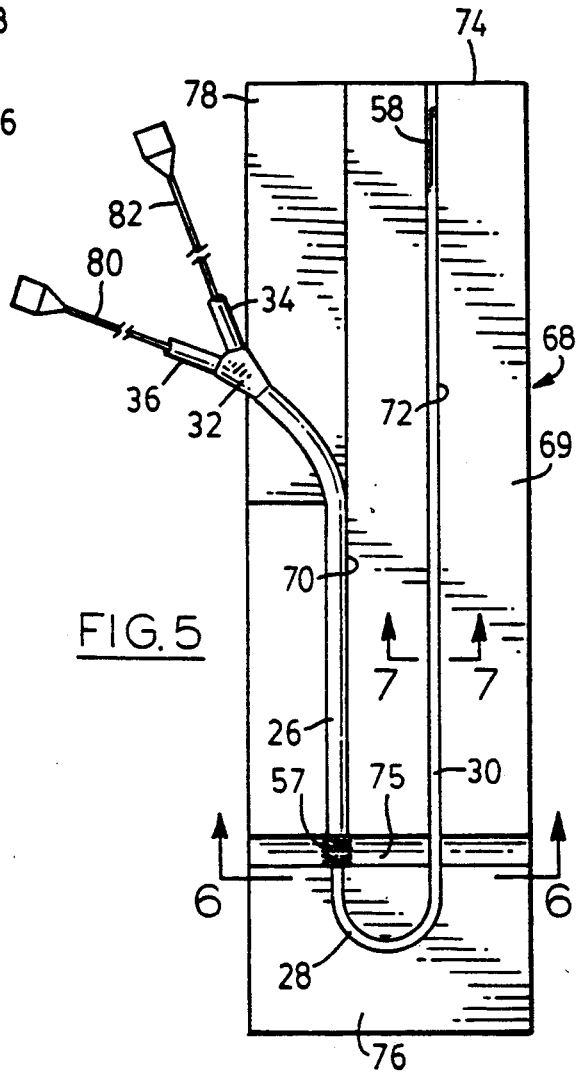
FIG. 5 is a top view of a fixture used in the manufacture of the catheter and illustrating a preferred method of manufacture.
Figure 6:
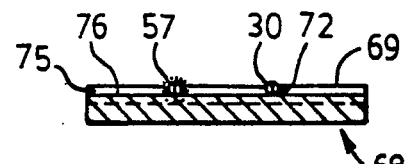
FIG. 6 is a sectional view on line 6—6 of FIG. 5.

Reference is now made to FIGS. 5 and 6, FIG. 6 being a sectional view on line 6—6 of FIG. 5. It will be seen that a simple fixture 68 is shown and is made essentially of a block of NYLON (registered trademark of DuPont) machined to provide a raised land 69 in which are formed a pair of parallel channels 70, 72. The channel 70 extends from an end 74 of the fixture 68 to a transverse channel 74 which is deeper than the channels 70, 72 and lies between the raised land 69 and a secondary land 76. The depth of the channels 70, 72 and proportions of the channels are selected so that the proximal portion 26, and distal portion 30 will engage snugly in the respective channels 70, 72 with the cuff 57 located in the transverse channel 74 and the portion to be curved 28 resting on the secondary land 76. A platform 78 is provided level with the bottom of channel 70 to support the coupling 32 and other parts simply as a matter of convenience.

The manufacture of the catheter will now be described with reference to FIG. 1. Firstly the tip 46 is formed on a selected length of extension 47 by first cutting off a section of the body 24 while leaving the septum and return lumen intact. The material is preferably medical grade polyurethane with a Durometer reading of 80 and the diameter is 11.5 French with an insertion length of 19 cm. The sleeve is of the same material and preferably with a wall thickness of 0.020 inches. A round mandrel is then placed in the portion between openings 60 and 66 and heat is applied using a shaped die to permanently deform the material into the tubular cylindrical extension 56. Next the openings 62 and 64 are machined in the catheter using a hollow drill.

As explained with reference to FIG. 2 the body portion 26 consists of the extrusion 47 which extends through out the length of the body and a sleeve 56 which fits snugly about the first part between the cuff 57 (FIG. 1) and the coupling 24. With reference to FIG. 1, the cuff 57 serves to cover the junction or exposed end of the sleeve 56 so that this end will not cause any interference in use. The cuff is preferably of fibrous DACRON (trade mark of E. I. DuPont for polyester material) and is adhered to the body. At the other end, the sleeve 56 blends into the moulded coupling 32. Similarly, the tubes 34, 36 also blend into the coupling where they are connected to the D-shaped lumens in the body 24.

Figure 7:
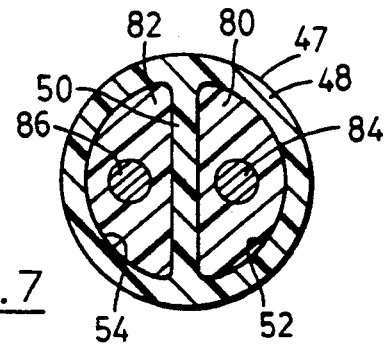
FIG. 7 is a sectional view on line 7—7 of FIG. 5 and drawn to a larger scale.

The resulting straight catheter must now be formed to give the curved section 28. A pair of D-shaped mandrels 80, 82 are slipped into the respective lumens 52, 54 and engage past the part which will form the curved portion 28 and into the distal portion 30. These mandrels have a cross-section shown in FIG. 7 where it will be seen that they fit snugly inside the lumens and consist of respective flexible steel cores 84, 86 surrounded by moulded TEFLON (trade mark) which has a low coefficient of friction inside the lumen to facilitate insertion and removal. Also the material resists temperatures needed to soften the extension 47.

Next, the fixture receives the proximal portion 26 with the cuff 57 engaged in the transverse channel 74 as a means of location relative to the length of the catheter. The body is then curved by hand and the distal portion 30 engaged in the channel 72 thereby forming the required shape of curved portion 28.

The curved portion 28 is then subject to boiling water which stress relieves the material and the portion 28 is set in the new shape by quenching with cold water. Although there is some energy retention stored by the mandrels and the extension, the resulting shape gives the curvature required in the preferred embodiment. Should a different curvature be required, the channels 70, 72 can be machined to diverge to the required angle. Some trial and error may be used to get this angle due to the slight memory retention of the assembly.

After cooling, the mandrels are withdrawn leaving the finished catheter.

The structure and method described may be varied within the scope of the invention claimed.

We claim:

1. A flexible catheter for prolonged vascular access, the catheter comprising: an elongate flexible and tubular body having a proximal portion, a distal portion and a permanently curved portion linking the proximal and distal portions so that the curved, the proximal and the distal portions lie naturally in essentially the same plane with the angle contained between the proximal and distal portions being less than 90°, and a septum extending continuously through said portions and lying substantially at right angles to said plane to divide the tubular body into generally D-shaped intake and outlet lumens; intake and outlet tubes coupled to the proximal portion at a proximal end of the body remote from the curved portion to receive incoming fluid from the intake lumen and to supply outgoing fluid to the outlet lumen; and a tip formed on the distal end of the distal portion and including at least one intake opening for receiving the incoming fluid and at least one outlet opening for returning the outgoing fluid.

2. A flexible catheter as claimed in claim 1 in which said portions are round in cross-section.

3. A flexible catheter as claimed in claim 2 in which the diameter of the proximal portion is greater than the diameter of the distal portion.

4. A flexible catheter as claimed in claim 3 and further comprising a cuff of fibrous material surrounding the body where the proximal portion meets the curved portion.

5. A flexible catheter as claimed in claim 2 and further comprising a cuff of fibrous material surrounding the body where the proximal portion meets the curved portion.

6. A flexible catheter as claimed in claim 1 and further comprising a cuff of fibrous material surrounding the body where the proximal portion meets the curved portion.

7. A flexible catheter as claimed in claim 1 in which the at least one intake opening at the end of the intake lumen and in which the tip includes a generally cylindrical extension blending smoothly into the body and forming an extension to the return lumen.

8. A flexible catheter as claimed in claim 7 in which the at least one intake opening is at a side of the distal portion facing the proximal portion, and in which the cylindrical extension is at a side of the distal portion remote from the proximal portion.

9. A flexible catheter as claimed in claim 8 in which said portions are round in cross-section.

10. A flexible catheter as claimed in claim 9 in which the diameter of the proximal portion is greater than the diameter of the distal portion.

11. A flexible catheter as claimed in claim 10 in which said angle is in the range of 0°-20°.

12. A flexible catheter as claimed in claim 8 and further comprising a cuff of fibrous material surrounding the body where the proximal portion meets the curved portion.

13. A flexible catheter as claimed in claim 1 in which the at least one intake opening is at a side of the distal portion facing the proximal portion, and in which the outlet opening is at a side of the distal portion remote from the proximal portion.

14. A flexible catheter as claimed in claim 13 in which said portions are round in cross-section.

15. A flexible catheter as claimed in claim 14 in which the diameter of the proximal portion is greater than the diameter of the distal portion.

16. A flexible catheter as claimed in claim 15 in which said angle is in the range of 0°-20°.

17. A flexible catheter as claimed in claim 13 and further comprising a cuff of fibrous material surrounding the body where the proximal portion meets the curved portion.

18. A flexible catheter as claimed in claim 1 in which the distal portion is sufficiently flexible to be deformed readily to follow the shape of a vein after entry, and in which the proximal portion is more rigid than the distal portion.

19. A flexible catheter as claimed in claim 1 in which said angle is in the range of 0° to 20°.

* * * * *